United States Patent
Gryska et al.

(10) Patent No.: US 9,562,872 B2
(45) Date of Patent: Feb. 7, 2017

(54) HUMIDITY SENSOR AND SENSOR ELEMENT

(71) Applicant: 3M INNOVATIVE PROPERTIES COMPANY, St. Paul, MN (US)

(72) Inventors: Stefan H. Gryska, Woodbury, MN (US); Krzysztof A. Lewinski, Mahtomedi, MN (US); Michael C. Palazzotto, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 235 days.

(21) Appl. No.: 14/399,381

(22) PCT Filed: May 13, 2013

(86) PCT No.: PCT/US2013/040709
§ 371 (c)(1),
(2) Date: Nov. 6, 2014

(87) PCT Pub. No.: WO2013/180936
PCT Pub. Date: Dec. 5, 2013

(65) Prior Publication Data
US 2015/0153296 A1 Jun. 4, 2015

Related U.S. Application Data

(60) Provisional application No. 61/652,496, filed on May 29, 2012.

(51) Int. Cl.
*G01N 27/22* (2006.01)
*G01N 27/12* (2006.01)

(52) U.S. Cl.
CPC .......... *G01N 27/223* (2013.01); *G01N 27/121* (2013.01); *G01N 27/225* (2013.01); *G01N 27/126* (2013.01)

(58) Field of Classification Search
CPC .. G01N 27/121; G01N 27/126; G01N 27/223; G01N 27/225; G01N 2201/1214
See application file for complete search history.

(56) References Cited

U.S. PATENT DOCUMENTS 4,520,341 A * 5/1985 Miyoshi ............... G01N 27/121
338/35
4,632,879 A 12/1986 Tanaka
(Continued)

FOREIGN PATENT DOCUMENTS

CN 101220120 7/2008
JP 57-202405 12/1982
(Continued)

OTHER PUBLICATIONS

Marisa C. Buzzeo et al., "Use of Room Temperature Ionic Liquids in Gas Sensor Design", Analytical Chemistry 2004, 76, 4583-4588.
(Continued)

*Primary Examiner* — Blake A Tankersley
(74) *Attorney, Agent, or Firm* — Yufeng Dong; Bradford B. Wright (57) ABSTRACT

A humidity sensor element includes a dielectric substrate, a nonporous conductive electrode disposed on the dielectric substrate, a permeable conductive electrode having a thickness in a range of from 4 to 10 nanometers and permeable by water vapor, and a detection layer disposed between the nonporous conductive electrode and the permeable conductive electrode. Both conductive electrodes have respective conductive leads attached thereto. The detection layer includes a sulfonated copolymer including monomeric units comprising (I) and (II), Wherein x and y are independently integers in the range of from 2 to 6, and wherein each M independently represents H or an alkali metal. A humidity sensor including the humidity sensor element is also disclosed.

(Continued)

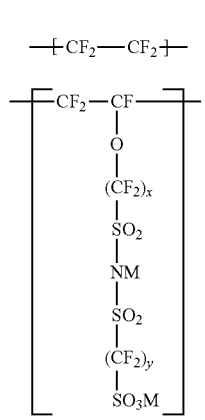

(I)
(II)

10 Claims, 1 Drawing Sheet

| | | | |
|---|---|---|---|
| 8,409,511 | B2 | 4/2013 | Thomas |
| 8,564,740 | B2 | 10/2013 | Schultz |
| 8,835,180 | B2 | 9/2014 | Gryska |

FOREIGN PATENT DOCUMENTS

| | | |
|---|---|---|
| JP | 59-091355 | 5/1984 |
| JP | 60-016451 | 1/1985 |
| JP | 61-176844 | 8/1986 |
| JP | H2-36344 | 2/1990 |
| WO | WO 2004-078830 | 9/2004 |
| WO | WO 2009-018009 | 2/2009 |
| WO | WO 2009-045733 | 4/2009 |
| WO | WO 2009-046011 | 4/2009 |
| WO | WO 2010-075333 | 7/2010 |
| WO | WO 2011-129967 | 10/2011 |
| WO | WO 2012-044419 | 4/2012 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2012-170248 | 12/2012 |

OTHER PUBLICATIONS

Yuan Gee Lee, et al., "Ionic Liquid Ethanol Sensor", Biosensors and Bioelectronics, 20 (2004) 33-40.
Guo et al. "CO Electrochemical Sensors with PVDF-g-PS/PASA Electrolyte Membrane", Journal of Materials Engineering, May 2010, 6 pages.
International Search Report for PCT International Application No. PCT/US2013/040709, mailed on Aug. 16, 2013, 4 pages.

(56) References Cited

U.S. PATENT DOCUMENTS

| | | | |
|---|---|---|---|
| 4,662,220 | A | 5/1987 | Laue |
| 4,954,238 | A | 9/1990 | Kato |
| 5,036,704 | A | 8/1991 | Pusatcioglu |
| 5,050,434 | A | 9/1991 | Demisch |
| 5,131,990 | A * | 7/1992 | Kulwicki ............ G01N 27/121 204/422 |

\* cited by examiner

HUMIDITY SENSOR AND SENSOR ELEMENT

FIELD

The present disclosure broadly relates to capacitance-type sensor elements and humidity sensors.

BACKGROUND

Humidity sensors are widely used in the monitoring and control of industrial processes, environmental applications, electronic and biotechnology sectors, agriculture, libraries and household applications. In the last few years an increasing demand has developed for low cost humidity sensors with high accuracy, good reproducibility and long-term stability. Unfortunately, good humidity sensors are very expensive and most of the inexpensive ones do not perform well at above 70 percent or below 20 percent relative humidity.

Capacitive humidity sensors have been constructed by sandwiching a humidity-sensitive material between two parallel electrodes. Sulfonated fluoropolymers have been used as the humidity-sensitive material because of their excellent thermal and mechanical stability, and the capability of extremely fast and accurate response to change in humidity.

One of the most widely used sulfonated fluoropolymers in construction of humidity sensors include copolymers of $CF_2=CFOCF_2CF(CF_3)OCF_2CF_2SO_3H$ and tetrafluoroethylene. Polymers of this type are available under the trade designation NAFION from E. I. du Pont de Nemours and Company of Wilmington, Del. For example, U.S. Pat. No. 4,662,220 (Laue) reports a method and apparatus using a known water-absorbent polymer as a capacitor which is operated at a DC voltage for measuring relative humidity. When formed as a layer between porous electrically-conductive electrodes and operated in an RC oscillator circuit, the oscillator frequency varies inversely with the partial pressure of the moisture to be measured. In a preferred embodiment, the capacitor is formed from a NAFION polymer.

U.S. Pat. No. 5,036,704 (Pusatcioglu et al.) reports a moisture sensor that utilizes a sulfonated fluorocarbon film having a thickness of less than about one micron and capable of providing accurate measurements of humidity and extremely fast response to change in humidity. A preferred embodiment of an electrical system is disclosed for use with the sensor, and a sulfonated tetrafluoroethylene perfluoroether copolymer form of the film is especially preferred.

SUMMARY

In one aspect, the present disclosure provides a humidity sensor element comprising:
a dielectric substrate;
a nonporous conductive electrode having a first conductive member electrically coupled thereto, wherein the nonporous conductive electrode is disposed on the dielectric substrate;
a permeable conductive electrode having a second conductive member electrically coupled thereto, wherein the permeable conductive electrode has a thickness in a range of from 4 to 10 nanometers, and wherein the permeable conductive electrode is permeable by water vapor;
a detection layer disposed between (e.g., sandwiched between) the nonporous conductive electrode and the permeable conductive electrode, wherein the detection layer comprises a sulfonated copolymer including monomeric units comprising wherein x and y are independently integers in the range of from 2 to 6 (i.e., 2, 3, 4, 5, or 6), and wherein each M independently represents H or an alkali metal (e.g., Li, Na, or K).

Humidity sensor elements according to the present disclosure are useful, for example, for incorporation into humidity sensors. Accordingly, in another aspect, the present disclosure provides a humidity sensor comprising:
a sensor chamber having an inlet opening;
a humidity sensor element according to the present disclosure and having a capacitance, wherein the humidity sensor element is disposed within the sensor chamber in fluid communication with the inlet opening; and
an operating circuit in electrical communication with the first and second conductive leads of the humidity sensor element, whereby if the humidity sensor element is connected to a source of electrical power, the operating circuit measures the capacitance of the sensor element.

Humidity sensor elements used in the present disclosure may have better reliability and/or durability, especially at elevated temperatures.

As used, herein the term "wherein the permeable conductive electrode is permeable by water vapor" means that water vapor is capable of passing through the bulk material comprising the conductive electrode for a distance of at least its full thickness, and does not refer to passage through perforations or other such intentionally provided openings in the conductive electrode.

As used herein, "sulfonate equivalent weight" refers to as the weight of the polymer (in grams) per mole of sulfonic acid and sulfonate groups combined.

Sulfonated fluoropolymer-based capacitive sensors may be very sensitive to change in humidity over the entire range of percent. They can be used, for example, in household applications to automatically turn on/off bathroom fan based on the relative humidity or in challenging industrial applications to monitor corrosive gases for their moisture level. These sensors offer good selectivity and permeability to water vapors and their response time is comparable to commercial units.

The features and advantages of the present disclosure will be further understood upon consideration of the detailed description as well as the appended claims.

In all cases, the disclosure is presented by way of representation and not limitation. It should be understood that numerous other modifications and embodiments can be devised by those skilled in the art, which fall within the scope and spirit of the principles of the disclosure. The figure may not be drawn to scale.

DETAILED DESCRIPTION

Figure 1:
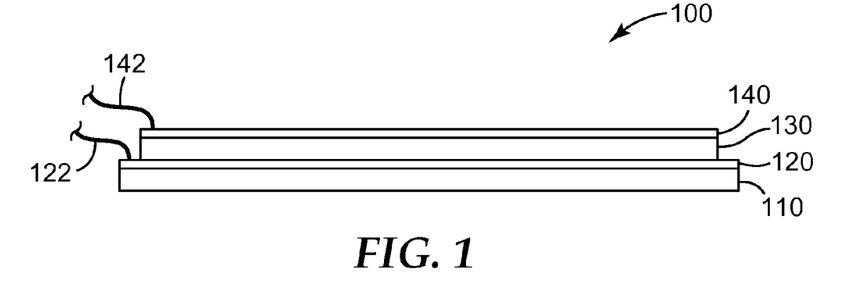
FIG. 1 is a schematic side view of an exemplary sensor element 100 according to the present disclosure.

Referring now to FIG. 1, exemplary humidity sensor element 100 comprises dielectric substrate 110, nonporous conductive electrode 120 disposed on substrate 110, permeable conductive electrode 140, and detection layer 130, disposed between nonporous conductive electrode 120 and permeable conductive electrode 140. First and second conductive members (122, 142) are electrically coupled to nonporous conductive electrode 120 and permeable conductive electrode 140, respectively. Permeable conductive electrode 140 has a thickness in a range of from 4 to 10 nanometers, and is permeable by water vapor. Detection layer 130 comprises a sulfonated copolymer including monomeric units comprising wherein x and y are independently integers in the range of from 2 to 6, and wherein each M independently represents H or an alkali metal.

Dielectric substrate 110 may comprise any dielectric material that may serve to provide physical strength and integrity to the sensor element. Suitable materials include glasses, ceramics, stone, minerals (e.g., alpha alumina or sapphire), thermoplastics (e.g., polyesters, polycarbonates, polyamides, polyimides, and polyether ether ketones) and thermosets (e.g., Bakelite and cured epoxy resins). In large scale production, a polymeric film (such as polyester) may be used. In some embodiments, the dielectric substrate is nonporous, although this is not a requirement as long as it can support the nonporous conductive electrode. Similarly, it is typically at least coextensive with the nonporous conductive electrode, although this is not a requirement as long as it can support the nonporous conductive electrode. In some embodiments, the dielectric substrate comprises a glass plate.

Nonporous conductive electrode 120 may comprise any conductive material, desirably a corrosion-resistant conductive material. Combinations of different materials (conductive and/or nonconductive) can be used, as different layers or as a mixture, as long as sufficient overall conductivity is provided. Typically, the nonporous conductive electrode has a sheet resistance of less than about $10^7$ ohms/square ($10^7$ $S^{-1}$/square), although higher sheet resistances may also be used. Examples of materials that can be used to make the nonporous conductive electrode include: organic materials, inorganic materials, metals and their alloys, and combinations thereof. In certain embodiments, coated (e.g., thermal-vapor-coated, sputter-coated) metals or metal oxides, or combinations thereof, may be used. Suitable conductive materials include for example aluminum, nickel, titanium, tin, indium-tin oxide, gold, silver, platinum, palladium, copper, chromium, carbon (e.g., including carbon nanotubes), and combinations thereof. In some embodiments, the conductive material is selected from titanium, gold, platinum, and combinations thereof. Desirably, to avoid corrosion, a noble metal component of the nonporous electrode is in contact with the detection layer.

The nonporous conductive electrode has a thickness in a range of from at least 4 nm to 400 nm, or from 10 nm to 200 nm.

Detection layer 120 comprises a sulfonated copolymer including monomeric units comprising wherein x and y are independently integers in the range of from 2 to 6, and wherein each M independently represents H or an alkali metal. In some embodiments, x is 3, 4, or 5, and y is 2, 3, or 4. In one embodiment, x is 4 and y is 3.

Such sulfonated copolymers and methods for their preparation are described, for example, in PCT Publ. No. WO 2011/129967 A2 (Hamrock et al.). In one embodiment, the sulfonated copolymer may be a random copolymer represented by the stoichiometric formula wherein m and n are positive integers (i.e., 1, 2, 3, etc.), and M is as previously defined. Other monomeric units having pendant groups such as, for example, perfluoroalkyl groups or perfluoroalkoxyl groups may also be present. Typically, substantially no (e.g., less than 5 mole percent of) other monomeric units having pendant groups are present in the sulfonated copolymer; and more typically, no other monomeric units having pendant groups are present.

The sulfonated copolymer may be made by the copolymerization of tetrafluoroethylene with a corresponding monomer having the formula $CF_2=CFO(CF_2)_xSO_2F$ wherein x is as previously defined. On exemplary such monomer is 4'-fluorosulfonyl-1',1',2',2',3',3',4',4'-octafluorobutyloxy-1,2,2-trifluoroethylene (i.e., $CF_2=CFO(CF_2)_4SO_2F$), for example, as described in U.S. Pat. No. 7,071,271 (Thaler et al.). The resulting polymer can then be reacted with a corresponding sulfonamide having the formula $MO_3S(CF_2)_ySO_2NHM$, wherein M and y are as previously defined. Further details concerning synthesis of useful monomers can be found in PCT Publ. No. WO 2011/129967 A2 (Hamrock et al.).

Additional co-monomers may be included to provide perfluoroalkyl or perfluoroalkyl ether pendant groups in the sulfonated copolymer. Vinylidene fluoride may also be used as a monomer. Polymerization can be accomplished by any suitable method, including aqueous emulsion polymerization. Typically, the sulfonated copolymer has a sulfonate equivalent weight in a range of from 570 to 10000 grams per sulfonate equivalent, preferably in a range of from 620 to 5000 grams per sulfonate equivalent, more preferably in a range of from 660 to 2000 grams per sulfonate equivalent, and more preferably in a range of from 800 to 1500 grams per sulfonate equivalent, although other sulfonate equivalent weights may also be used. In some embodiments, the sulfonated copolymer has a sulfonate equivalent weight in a range of from 1000 to 1300 grams per sulfonate equivalent.

The detection layer may be deposited (for example, on the nonporous conductive layer) by any suitable technique. Casting out of solvent or water, followed by heating to dry and optionally anneal the detection layer is typically an effective method. If desired, a fluorosulfonylated precursor copolymer may be cast out of solvent followed by hydrolysis, as discussed above.

The detection layer may have any thickness, but typically is in a range of from about 100 nanometers (nm) to 1 millimeter. More typically, the detection layer has a thickness in a range of from 500 nm to 10 microns, or even from 700 to 3500 nm.

The detection layer may contain additional additives such as, for example, colorants, residual organic solvent, fillers, or plasticizers; however, as such additives may be detrimental, the detection layer typically consists essentially (or consists) of the above-described sulfonated copolymer.

Permeable conductive electrode 140 is permeable to water vapor and conductive. Typically, permeable conductive electrode has a sheet resistance of less than about $10^7$ ohms/square ($10^7$ $S^{-1}$/square), although higher sheet resistances may also be used.

In some embodiments, the permeable conductive electrode comprises at least one noble metal (e.g., gold, platinum, palladium, or a combination thereof). In some embodiments, the permeable conductive electrode may have a noble metal content of at least 50, 60, 70, 80, 90, 95, 99, or even at least 99.9 percent by weight. In some embodiments, the permeable conductive electrode consists of, or consists essentially of gold, palladium, platinum, or a combination thereof. The second layer may include additional components as long as it remains permeable to water vapor. Combinations of different materials (conductive and/or nonconductive) can be used, as different layers or as a mixture, as long as sufficient overall conductivity and permeability is provided. Typically, the permeable conductive electrode has a sheet resistance of less than about $10^7$ ohms/square ($10^7$ $S^{-1}$/square).

The permeable conductive electrode has a thickness in a range of from 4 to 10 nanometers (nm). In some embodiments, the permeable conductive electrode has a thickness in a range of from 5, 6, or 7 nm up to 8, 9, or 10 nm. For example, the permeable conductive electrode may have a thickness in a range of from 5 nm to 8 nm, or from 6 nm to 7 nm. Greater thicknesses generally have undesirably low levels of permeability, while lesser thicknesses may become insufficiently conductive and/or difficult to electrically connect to the second conductive member. Since the permeable conductive electrode is permeable, the first electrode typically comprises a continuous, uninterrupted layer, but it may contain openings or other interruptions if desired.

The permeable conductive electrode can be prepared by a thermal vapor deposition process. In thermal vapor deposition, the material used to make the permeable conductive electrode is heated under vacuum until it vaporizes and deposits on an appropriate component of the humidity sensor element (e.g., detection layer 130). Any suitable source of heating may be used; examples include resistive heating, laser heating, and e-beam heating (also termed e-beam evaporation). Thermal vapor deposition is generally carried out at pressures of about $10^{-5}$ or $10^{-6}$ torr (1 mPa-0.1 mPa) or less.

Thermal vapor deposition differs from sputter deposition. In sputter deposition, high energy atoms are bombarded into a target or source which then ejects material that deposits on a substrate. Typical pressures involved in sputter deposition are in the range of $10^{-4}$-$10^{-2}$ torr (0.0133 Pa-1.33 Pa) or higher.

The nonporous conductive electrode and the permeable conductive electrode are separated from (e.g., not in physical contact with) each other by at least the detection layer. Typically, the nonporous conductive electrode and the permeable conductive electrode are arranged in a parallel configuration (e.g., as in the case of a sandwich configuration) or an interdigitated configuration, however other configurations are also permitted.

First and second conductive members (122, 142) may be formed of any conductive material such as, for example, metal (e.g., gold or copper), carbon, and/or conductive oxide. First and second conductive members (122, 142) may comprise, for example, wires, traces, or a combination thereof. They may be electrically coupled to the permeable and nonporous conductive electrodes at any appropriate point during assembly of the sensor element. For example, the first conductive member 122 may be attached to the nonporous conductive electrode 120 immediately after deposition of the nonporous conductive electrode and before deposition of the detection layer.

Figure 2:
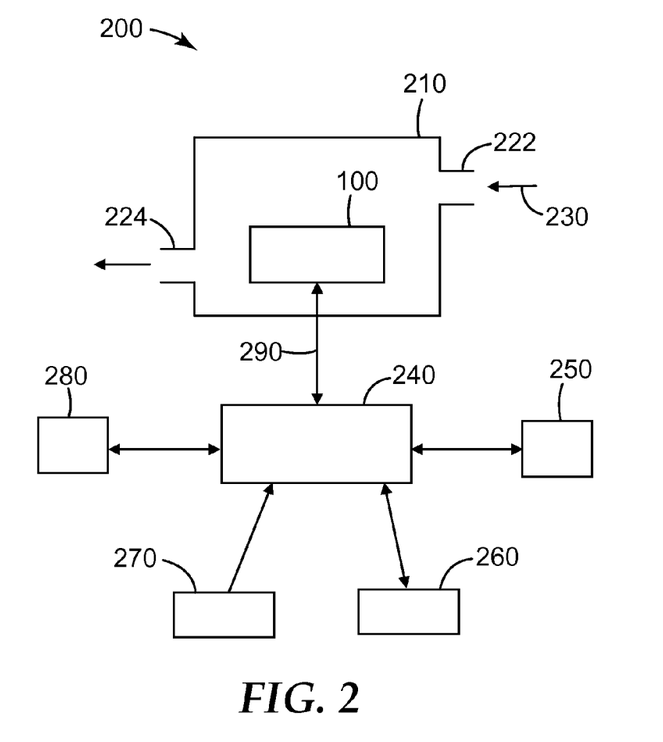
FIG. 2 is a schematic plan view of an exemplary humidity sensor 200 according to the present disclosure.

Referring now to FIG. 2, exemplary humidity sensor 200 includes a sensor chamber 210 having an inlet opening 222 and optional outlet opening 224. Humidity sensor element 100 (as described hereinabove) is disposed within the sensor chamber 210, and is in fluid communication with the inlet opening 222 and optional outlet opening 224, if present. In typical operation, a sample containing water vapor 230 enters sensing chamber 210 where it contacts humidity sensor element 100. Operating circuit 240 is in electrical communication via conductive pathways 290 with humidity sensor element 100. When connected to a source of electrical power 270, operating circuit 240 measures the capacitance of humidity sensor element 100. In some embodiments, operating circuit 240 is communicatively coupled to data storage device 250, controller device 280, and/or display device 260.

Operating circuit 240 can have any suitable design, for example, as will be known to those of skill in the art. For example, the operating circuit may comprise an LCR meter, a multimeter, or other electronic measurement device.

In operation, the operating circuit 240 is in electrical communication with a source of electrical power 270.

Exemplary sources of electrical power include batteries, plug in power supplies, generators, hardwired power supplies, and RF generators (e.g., if the operating circuit includes an RF receiver).

The sensor chamber can be constructed of any solid material that is impermeable to the water vapor. Examples include metal and/or plastic. Exemplary display devices 260 include LED displays, LCD displays, CRT displays, galvanic meters, and printers. Controller device 280, if present, includes hardware and/or software that directs operation of the operating circuit. Exemplary data storage devices 250 include flash memory cards, hard disks, digital tape, and CD-R media.

Humidity sensor elements and sensor devices according to the present disclosure can be used to detect and/or monitor (e.g., qualitatively or quantitatively) humidity levels of air, and may also be used to detect other analytes that are adsorbed/absorbed by the detection layer.

Upon absorption of sufficient water vapor by the detection layer, a detectable change in an electrical property associated with the humidity sensor element (e.g., capacitance, impedance, inductance, admittance, current, or resistance) may occur. Such a detectable change may be detected by an operating circuit that is in electrical communication with the nonporous conductive electrode and the permeable conductive electrode. In this context, "operating circuit" refers generally to an electrical apparatus that can be used to apply a voltage to the nonporous conductive electrode and the permeable conductive electrode (thus imparting a charge differential to the electrodes), and/or to monitor an electrical property of the sensor element, wherein the electrical property may change in response to the presence of water vapor. In various embodiments, the operating circuit may monitor any or a combination of inductance, capacitance, voltage, resistance, conductance, current, impedance, phase angle, loss factor, or dissipation.

Such an operating circuit may comprise a single apparatus which both applies voltage to the electrodes, and monitors an electrical property. In an alternative embodiment, such an operating circuit may comprise two separate apparatuses, one to provide voltage, and one to monitor the signal. The operating circuit is typically electrically coupled to nonporous conductive electrode and the permeable conductive electrode by the first and second conductive members.

Humidity sensor elements according to the present disclosure are useful, for example, as sensor elements in humidity sensors, for example, as discussed above.

SELECT EMBODIMENTS OF THE PRESENT DISCLOSURE

In a first embodiment, the present disclosure provides a humidity sensor element comprising:
a dielectric substrate;
a nonporous conductive electrode having a first conductive member electrically coupled thereto, wherein the nonporous conductive electrode is disposed on the dielectric substrate;
a permeable conductive electrode having a second conductive member electrically coupled thereto, wherein the permeable conductive electrode has a thickness in a range of from 4 to 10 nanometers, and wherein the permeable conductive electrode is permeable by water vapor;
a detection layer disposed between the nonporous conductive electrode and the permeable conductive electrode, wherein the detection layer comprises a sulfonated copolymer including monomeric units comprising wherein x and y are independently integers in the range of from 2 to 6, and wherein each M independently represents H or an alkali metal.

In a second embodiment, the present disclosure provides a humidity sensor element according to the first embodiment, wherein the dielectric substrate is nonporous.

In a third embodiment, the present disclosure provides a humidity sensor element according to the first or second embodiment, wherein the dielectric substrate comprises a glass plate.

In a fourth embodiment, the present disclosure provides a humidity sensor element according to any one of the first to third embodiments, wherein the permeable conductive electrode comprises gold.

In a fifth embodiment, the present disclosure provides a humidity sensor element according to any one of the first to fourth embodiments, wherein the nonporous conductive electrode comprises gold.

In a sixth embodiment, the present disclosure provides a humidity sensor element according to any one of the first to fifth embodiments, wherein the sulfonated copolymer is a random copolymer including a segment represented by the stoichiometric formula wherein m and n are positive integers, and each M is independently H or an alkali metal.

In a seventh embodiment, the present disclosure provides a humidity sensor element according to any one of the first to sixth embodiments, wherein the sulfonated copolymer has a sulfonate equivalent weight in a range of from 660 to 2000 grams per sulfonate equivalent.

In an eighth embodiment, the present disclosure provides a humidity sensor comprising:

a sensor chamber having an inlet opening;

a humidity sensor element according to any one of the first to seventh embodiments and having a capacitance, wherein the humidity sensor element is disposed within the sensor chamber in fluid communication with the inlet opening; and an operating circuit in electrical communication with the first and second conductive leads of the humidity sensor element, whereby if the humidity sensor element is connected to a source of electrical power, the operating circuit measures the capacitance of the sensor element.

In a ninth embodiment, the present disclosure provides a humidity sensor according to the eighth embodiment, wherein the sensor chamber further comprises an outlet opening in fluid communication with the inlet opening.

In a tenth embodiment, the present disclosure provides a humidity sensor element according to the eighth or ninth embodiment, further comprising a display device communicatively coupled with the operating circuit.

Objects and advantages of this disclosure are further illustrated by the following non -limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

General Procedure for Preparation of Sensor Elements

Glass slides (glass number 0050-0050-0010-GF-CA, 50 mm×50 mm, 1.1 mm thick, material C-263, surface 80/50, from Precision Glass & Optics, Santa Ana, Calif.) were cleaned by soaking for 30-60 minutes in ALCONOX LIQUI-NOX detergent solution from Alconox, Inc., White Plains, N.Y., then scrubbing each side of the slides with a bristle brush, rinsing under warm tap water followed by a final rinse with deionized water. The slides were allowed to air dry covered to prevent dust accumulation on the surface. The dry, clean slides were stored in 3-inch (7.6-cm) wafer carriers from Entegris, Chaska, Minn.

Nonporous conductive electrodes were deposited onto the clean glass slides by thermal vapor coating 5.0 nanometers (nm) of titanium followed by 20.0 nm of gold using a square mask (MASK A) having a single rectangular opening with a top border of 0.46 inch (1.2 cm), a bottom border of 0.59 inch (1.5 cm), and left and right borders of 0.14 inch (0.35 cm) prepared from laser-cut 1.16 mm thick stainless steel. The deposition process was controlled using an INFICON XTC/2 THIN FILM DEPOSITION CONTROLLER from INFICON, East Syracuse, N.Y.

Next, the nonporous conductive electrodes were spin coated with a solution/dispersion of sulfonated fluoropolymer using a Model WS 400B-8NPP/LITE spin coater from Laurell Technologies Corporation, North Wales, Pa. Each specimen to be coated was placed in the spin coater and about 0.5 ml of methanol was placed on the sample. Each sample was spun for 60 seconds at a specific rotational speed (rpm) as indicated. Then, for all specimens, about one mL of sulfonated fluoropolymer solution/dispersion was dispensed on the sample and spun for 60 seconds at specific rpm (see examples). After spin coating, thickness measurements of the sulfonated fluoropolymer (i.e., detection layer) were made using a Model XP-1 Profilometer from AMBiOS Technology of Santa Cruz, Calif. All samples were baked for one hour at 150° C. after coating.

The permeable conductive electrode was vapor deposited through a 2 inches (5 cm)×2 inches (5 cm) mask (MASK B) having a 2×2 regular array of four 0.60 inch (1.5 cm) height×0.33 inch (0.84 cm) width rectangular openings vertically separated by 0.22 inch (0.56 cm) and horizontally separated by 0.48 inch (1.2 cm) was made from 24 gauge stainless steel by laser milling using thermal deposition of gold at 6 nm thickness (Comparative Example A) or 7 nm thickness (Example 1). After depositing the permeable conductive electrode, connecting electrodes were deposited by thermal vapor coating 5.0 nm of titanium followed by 20.0 nm of gold (Comparative Example A) or 50 nm single layer of gold (Example 1) through a 2 inches (5 cm)×2 inches (5 cm) mask (MASK C) having two horizontal rectangular openings with a height of 0.4 inch (1 cm), left and right borders of 0.14 inch (0.36 cm), and a separation of 0.92 inch (2.4 cm), prepared by laser milling from 50 gauge stainless. The deposition process was controlled using an INFICON XTC/2 THIN FILM DEPOSITION CONTROLLER.

This sensor element preparation process produced a set of 4 specimens of approximately 5 mm×6 mm active area (area disposed between the permeable conductive electrode and the nonporous conductive electrode) disposed on an approximately 50 mm×50 mm glass substrate. Individual specimens were produced by dicing the specimen using a standard glass scoring cutter on the back (inactive side) while supporting the specimens so that their front (active) surfaces would not be damaged. After dicing, individual specimens were tested for electrical shorts using a Protek multimeter (Model 6300 5 in 1, Digital Multimeter, obtained from Protek Test and Measurement of Englewood, N.J.).

All tests were performed in air that had been passed over DRIERITE desiccant from W.A. Hammond Drierite Co. Ltd., Xenia, Ohio to remove moisture, and passed over activated carbon to eliminate organic contaminates. Vapor tests were conducted with the specimen disposed within in test chamber into which air having varying levels of relative humidity was introduced.

Percent Relative Humidity (% RH) Capacitance Response Testing

Sensor element specimens were tested for response to various levels of relative humidity at ambient temperature. A simple flow-through delivery system was used to deliver known levels of relative humidity to the capacitive sensor for measurement. Polytetrafluoroethylene (PTFE) tubing was used throughout the delivery system. The exposure concentrations were generated by 10 L/min flow of air through temperature-controlled evaporation flask containing distilled water. The temperature of the water in the double wall flask was controlled by a Heating/Cooling Circulator from VWR and the air stream of dry air was regulated by a Matheson gas flow meter. The relative humidity in the gaseous stream was monitored with an iTHX-M Humidity Meter available from Omega Engineering Inc., Stamford, Conn. The humidified air was introduced into a test chamber (held at controlled temperature) containing the humidity sensor (prepared above). The electrodes of the humidity sensor were connected to an operating circuit that comprised an LCR meter (available as Instek Model 821 LCR meter from Instek America, Corp. Chino, Calif.) using spring loaded probes. The changes in capacitance (in picofarads (pF)) of the capacitive sensor were monitored at a frequency of 1 kHz and 1 V at specific time intervals during the entire course of the water vapor test. The choice of such low operating potential and high perturbation frequency ensured lack of interference from any possible Faradaic processes associated with electrolyzing water present in the measured gas stream.

Comparative Example A

Comparative Example A was prepared according to the GENERAL PROCEDURE FOR PREPARATION OF SENSOR ELEMENTS using 20.0 percent solids by weight of 3M PERFLUOROSULFONIC ACID IONOMER (825 grams per sulfonate equivalent, available from 3M Company, Saint Paul, Minn.) copolymer in 60/40 (wt./wt.) n-propanol/water solution. 3M PERFLUOROSULFONIC ACID IONOMER is a polymer of tetrafluoroethylene and 4-sulfonatoperfluorobutoxy-trifluoroethylene (i.e., $CF_2=CFO(CF_2)_4SO_3H$).

Spin coating was done at 8000 rpm resulting in a 2191 nm thick detection layer. Before testing, the specimen (Comparative Example A) was placed in an oven for 15 minutes at 150° C. The specimen (Comparative Example A) was evaluated by attaching spring clip probes of an Instek Model 821 LCR meter to the nonporous conductive electrode and the permeable conductive electrode.

Measured humidity using an Omega iTHX-M Humidity Meter, and measured capacitance values for Comparative Example A and Example 1 under the same conditions are reported in the Table 1.

Example 1

Example 1 was prepared generally in the same way as Comparative Example A, except that Polymer A, a random sulfonated copolymer having the stoichiometric formula was used in place of the 3M PERFLUOROSULFONIC ACID IONOMER. Polymer A had a sulfonate equivalent weight of 1120 grams per sulfonate equivalent, corresponding to essentially the same number of sulfonate groups per tetrafluoroethylene units as in 3M PERFLUOROSULFONIC ACID IONOMER used in Comparative Example A. Polymer A was prepared generally according to the procedure given in Example 3 of PCT Publ. No. WO 2011/129967 A2 (Hamrock et al.).

Spin coating conditions of Example 1 were modified to achieve similar detection layer thickness. A 17.5 percent solids by weight solution of Polymer A was prepared in 80/20 (wt./wt.) methanol/water. Spin coating was done at 2500 rpm resulting in a 2190 nm thick detection layer. Before testing, the specimen (Example 1) was placed in an oven for 15 min at 150° C. The specimen (Example 1) was evaluated by attaching spring clip probes of an Instek Model 821 LCR meter to the nonporous conductive electrode and the permeable conductive electrode. Humidity exposure showed very good sensitivity, with much greater response than Comparative Example A. Measured percent relative humidity (% RH) using the Omega iTHX-M Humidity Meter, and measured capacitance values for Comparative Example A and Example 1 under the same conditions are reported in the Table 1 (below).

TABLE 1

| Omega Meter, % RH | CAPACITANCE, picofarads (pF) | |
|---|---|---|
| | COMPARATIVE EXAMPLE A | EXAMPLE 1 |
| 0 | 1.4 | 1.9 |
| 1.9 | 1.6 | 2.7 |
| 7.6 | 2.7 | 12.2 |
| 15.7 | 6.7 | 54.8 |
| 25.4 | 23.5 | 165.9 |
| 33.6 | 63.4 | 323.6 |
| 43.8 | 154.8 | 616.8 |
| 56.4 | 373.1 | 1225.6 |
| 70.4 | 906.8 | 2452.9 |
| 80.4 | 1967.3 | 3856.7 |
| 72.4 | 1337.3 | 2976.3 |
| 59.1 | 694.4 | 1637.4 |
| 46.2 | 312.8 | 859.0 |
| 36.4 | 114.2 | 477.4 |
| 27.7 | 57.1 | 243.5 |
| 18.7 | 12.8 | 93.4 |

All patents and publications referred to herein are incorporated by reference in their entirety. Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A humidity sensor element comprising:

a dielectric substrate;

a nonporous conductive electrode having a first conductive member electrically coupled thereto, wherein the nonporous conductive electrode is disposed on the dielectric substrate;

a permeable conductive electrode having a second conductive member electrically coupled thereto, wherein the permeable conductive electrode has a thickness in a range of from 4 to 10 nanometers, and wherein the permeable conductive electrode is permeable by water vapor;

a detection layer disposed between the nonporous conductive electrode and the permeable conductive electrode, wherein the detection layer comprises a sulfonated copolymer including monomeric units comprising wherein m and n are positive integers, and each M is independently H or an alkali metal.

7. The humidity sensor element of claim 1, wherein the sulfonated copolymer has a sulfonate equivalent weight in a range of from 660 to 2000 grams per sulfonate equivalent.

8. A humidity sensor comprising:
a sensor chamber having an inlet opening;
a humidity sensor element according to claim 1 and having a capacitance, wherein the humidity sensor element is disposed within the sensor chamber in fluid communication with the inlet opening; and
an operating circuit in electrical communication with the first and second conductive leads of the humidity sensor element, whereby if the humidity sensor element is connected to a source of electrical power, the operating circuit measures the capacitance of the sensor element.

9. The humidity sensor of claim 8, wherein the sensor chamber further comprises an outlet opening in fluid communication with the inlet opening.

10. The humidity sensor of claim 8, further comprising a display device communicatively coupled with the operating circuit.

wherein x and y are independently integers in the range of from 2 to 6, and wherein each M independently represents H or an alkali metal.

2. The humidity sensor element of claim 1, wherein the dielectric substrate is nonporous.

3. The humidity sensor element of claim 1, wherein the dielectric substrate comprises a glass plate.

4. The humidity sensor element of claim 1, wherein the permeable conductive electrode comprises gold.

5. The humidity sensor element of claim 1, wherein the nonporous conductive electrode comprises gold.

6. The humidity sensor element of claim 1, wherein the sulfonated copolymer is a random copolymer including a segment represented by the stoichiometric formula

\* \* \* \* \*

UNITED STATES PATENT AND TRADEMARK OFFICE
CERTIFICATE OF CORRECTION

PATENT NO. : 9,562,872 B2
APPLICATION NO. : 14/399381
DATED : February 7, 2017
INVENTOR(S) : Stefan Gryska et al.

It is certified that error appears in the above-identified patent and that said Letters Patent is hereby corrected as shown below:

In the Specification

Column 4
Lines 50-65 (approx.), Delete "" and insert --  --, therefor.

Signed and Sealed this
Thirteenth Day of June, 2017

Joseph Matal
*Performing the Functions and Duties of the
Under Secretary of Commerce for Intellectual Property and
Director of the United States Patent and Trademark Office*

Column 8
Lines 48-61 (approx.), Delete

"," and insert -- " --, therefor.

Column 9
Line 24, Delete "non -limiting" and insert -- non-limiting --, therefor.

Column 11
Lines 38-52, Delete

";" and insert --  --, therefor.

In the Claims

Column 14
Lines 1-14 (approx.), In Claim 6, Delete
"  ," and insert --  --, therefor.